US006436383B2

United States Patent
Murray

(10) Patent No.: US 6,436,383 B2
(45) Date of Patent: *Aug. 20, 2002

(54) SHAMPOO COMPOSITIONS

(75) Inventor: Andrew Malcolm Murray, Wiral (GB)

(73) Assignee: Unilever Home & Personal Care USA, division of Conopco, Inc., Chicago, IL (US)

(*) Notice: Subject to any disclaimer, the term of this patent is extended or adjusted under 35 U.S.C. 154(b) by 17 days.

This patent is subject to a terminal disclaimer.

(21) Appl. No.: 09/726,893

(22) Filed: Nov. 30, 2000

Related U.S. Application Data

(62) Division of application No. 09/262,529, filed on Mar. 4, 1999.

(30) Foreign Application Priority Data

Mar. 5, 1998 (GB) .............................................. 9804720

(51) Int. Cl.$^7$ ............................. A61K 7/06; A61K 7/11; A61K 7/075; A61K 7/08
(52) U.S. Cl. ............................... 424/70.122; 424/70.1; 424/70.12; 424/70.13; 424/70.27
(58) Field of Search ............................ 424/70.1–70.3, 424/70.27, 70.28, 70.12, 70.122, 70.13

(56) References Cited

U.S. PATENT DOCUMENTS

| | | | |
|---|---|---|---|
| 5,085,857 A | | 2/1992 | Reid et al. |
| 5,198,209 A | | 3/1993 | Zhou et al. |
| 5,306,434 A | | 4/1994 | Schueller et al. |
| 5,759,530 A | * | 6/1998 | Riccio et al. |
| 5,849,310 A | * | 12/1998 | Trinh et al. |
| 5,876,705 A | * | 3/1999 | Uchiyama et al. |
| 6,194,363 B1 | * | 2/2001 | Murray ...................... 510/119 |

FOREIGN PATENT DOCUMENTS

| | | | |
|---|---|---|---|
| EP | 0413416 A2 | 2/1991 | |
| EP | 0529883 | * 1/1997 | ............ A61K/7/00 |
| EP | 0811371 | 10/1997 | |
| GB | 2170216 | 7/1986 | |
| WO | 92/08439 | 5/1992 | |
| WO | 92/10162 | 6/1992 | |

OTHER PUBLICATIONS

Search Report under Section 17 Application No. GB 9804720.2 dated May 22, 1998.
Derwent Abstract No. 96–439443/199644 relating to JP 820017644 (8/96) assigned to Kao Corp.
Derwent Abstract No. 94–124076/199415 relating to JP 600072829 (3/94) assigned to Kao Corp.
Derwent Abstract No. 93–410766/199351 relating to JP 530010539 (11/93) assigned to Kao Corp.

* cited by examiner

Primary Examiner—Thurman K. Page
Assistant Examiner—Robert M. Joynes
(74) Attorney, Agent, or Firm—Matthew Boxer

(57) ABSTRACT

The conditioning performance of small particle size emulsified silicone in a surfactant-based shampoo composition can be significantly boosted by the inclusion in the shampoo composition of an amino functionalised silicone. Accordingly, the invention provides an aqueous shampoo composition comprising, in addition to water:

i) at least one surfactant chosen from anionic, nonionic, zwitterionic or amphoteric surfactants or mixtures thereof;

ii) an amino functionalised silicone; and iii) emulsified particles of an insoluble, non-amino functionalised silicone, in which the average silicone particle size of the emulsified non-amino functional silicone in the shampoo composition is less than 2 microns.

14 Claims, No Drawings

SHAMPOO COMPOSITIONS

This application is a division of Ser. No. 09/262,529 filed Mar. 4, 1999.

FIELD OF THE INVENTION

This invention relates to shampoo compositions, and more particularly to shampoo compositions containing emulsified particles of silicone, which compositions condition the hair leaving it softer and more manageable.

BACKGROUND AND PRIOR ART

The use of silicones as conditioning agents in cosmetic formulations is well known and widely documented in the patent literature. Generally, dispersed droplets of the silicone oil are suspended in the composition, which is then applied to the hair to deposit the silicone material on the hair shaft.

A typical method of silicone shampoo manufacture is disclosed in WO 92/10162. Essentially, the silicone material is emulsified directly into the shampoo by an in situ hot process, in which the complete shampoo mixture incorporating the silicone is mixed thoroughly at elevated temperature, pumped through a high shear mill and then cooled. The silicone can be dispersed in a first process stage with anionic surfactant and fatty alcohol to form a premix. The premix is then mixed with the remaining materials of the shampoo, pumped through a high shear mill, and cooled to obtain the final composition.

A disadvantage associated with an in situ hot process such as is described in WO 92/10162 is that factory handling of viscous silicone oil is difficult in the context of a full shampoo manufacturing operation.

A further disadvantage is that special equipment is normally needed to control silicone particle size during manufacture. GB 2 170 216 A discloses a similar process, in which the full shampoo composition incorporating insoluble, non-volatile silicone is sheared with a high shear mixer until the silicone particles are on average less than 2 microns in diameter. The particle size distribution is then said to be from about 2 to about −55 microns.

In order to solve the above mentioned problems with in situ hot processing of silicone, the alternative of incorporating the silicone as a preformed aqueous emulsion has been proposed. Such a method has the consequences that the silicone is incorporated with a predeterminable, controllable particle size distribution. The silicone is insoluble and remains emulsified in the fully formulated shampoo composition, and thus the step of high shear processing of the silicone within the fully formulated shampoo composition is not required. This also makes manufacture of the compositions easier.

A typical method for incorporating insoluble, non-volatile silicone materials into a conditioning shampoo is disclosed in U.S. Pat. No. 5,085,857 in which such materials are incorporated in the shampoo composition as a pre-formed aqueous emulsion of average particle size less than 2 microns. All the ingredients are mixed in a simple hot or cold process in which the average particle size of the silicone material in the emulsion remains the same in the final shampoo composition. Preferably, this size is from 0.01 to 1 micron, e.g. 0.4 micron.

EP 0 529 883 A1 discloses hair shampoo compositions made by an equivalent method and comprising microemulsified particles of silicone having a particle size of 0.15 microns or less, e.g., 0.036 microns. Reducing the silicone particle size still further in this way is said to improve stability, optical properties and conditioning performance.

A problem encountered with these small particle size silicone formulations is that the conditioning performance may be insufficient for many people, particularly in regions such as Japan and South East Asia where consumers desire a high level of conditioning and a "weighty" feel to their hair.

We have now found that the conditioning performance of small particle size emulsified silicone in a surfactant-based shampoo composition can be significantly boosted by the inclusion in the shampoo composition of an amino functionalised silicone.

U.S. Pat. No. 5,198,209 (Amway Corp) and L'Oreal EP 0 811 371 disclose conditioning shampoos with cleansing surfactant and a combination of dimethicone and trimethylsilylamodimethicone. The exemplified compositions use dimethicone fluid such as DC200 (60,000 cst). The dimethicone fluid is added directly to the shampoo as neat silicone oil of unspecified silicone particle size.

SUMMARY OF THE INVENTION

The invention provides an aqueous shampoo composition comprising, in addition to water:
 i) at least one surfactant chosen from anionic, nonionic, zwitterionic or amphoteric surfactants or mixtures thereof;
 ii) an amino functionalised silicone; and
 iii) emulsified particles of an insoluble, non-amino functionalised silicone, in which the average silicone particle size of the emulsified non-amino functional silicone in the shampoo composition is less than 2 microns.

DETAILED DESCRIPTION OF THE INVENTION

Surfactant

The composition according to the invention comprises a surfactant chosen from anionic, nonionic, zwitterionic or amphoteric surfactants or mixtures thereof.

Suitable anionic surfactants include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauroyl isethionate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Nonionic surfactants suitable for use in compositions of the invention may include condensation products of aliphatic ($C_8$–$C_{18}$) primary or secondary linear or branched chain alcohols or phenols with alkylene oxides, usually ethylene oxide and generally having from 6 to 30 ethylene oxide groups. Other suitable nonionics include mono- or di-alkyl alkanolamides. Example include coco mono- or di-ethanolamide and coco mono-isopropanolamide.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

Generally, the surfactants are present in shampoo compositions of the invention in an amount of from 0.1 to 50%, preferably from 5 to 30%, more preferably from 10% to 25% by weight.

Amino Functionalised Silicone

By "amino functionalised silicone" is meant a silicone containing at least one primary, secondary or tertiary amine group, or a quaternary ammonium group.

Examples Include (i) polysiloxanes having the CTFA designation "amodimethicone", and the general formula:

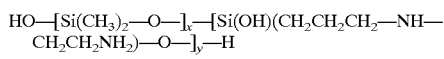

in which x and y are numbers depending on the molecular weight of the polymer, generally such that the molecular weight is between about 5,000 and 500,000.

(ii) polysiloxanes having the general formula:

in which:

G is selected from H, phenyl, OH or $C_{1-8}$ alkyl, e.g. methyl;

a is 0 or an integer from 1 to 3, preferably 0;

b is 0 or 1, preferably 1;

m and n are numbers such that (m+n) can range from 1 to 2000, preferably from 50 to 150;

m is a number from 1 to 2000, preferably from 1 to 10;

n is a number from 0 to 1999, preferably from 49 to 149, and

R' is a monovalent radical of formula —$C_qH_{2q}$L in which q is a number from 2 to 8 and L is an aminofunctional group selected from the following:

—NR"—$CH_2$—$CH_2$—N (R")$_2$
—N(R")$_2$
—N$^+$(R")$_3$A$^-$
—N$^+$H(R")$_2$A$^-$
—N$^+$H$_2$(R")A$^-$
—N(R")—$CH_2$—$CH_2$—N$^+$H$_2$(R")A$^-$ in which R' is selected from H, phenyl, benzyl, or a saturated monovalent hydrocarbon radical, e.g. $C_{1-20}$ alkyl, and A is a halide ion, e.g. chloride or bromide.

Suitable amino functionalised silicones corresponding to the above formula include those polysiloxanes termed "trimethylsilylamodimethicone" as depicted below, and which are sufficiently water insoluble so as to be useful in compositions of the invention:

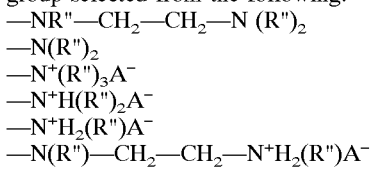

wherein x+y is a number from about 50 to about 500, and wherein R is an alkylene group having from 2 to 5 carbon atoms. Preferably, the number x+y is in the range of from about 100 to about 300.

(iii) quaternary silicone polymers having the general formula:

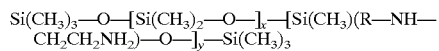

wherein $R^1$ and $R^{10}$ may be the same or different and may be independently selected from H, saturated or unsaturated long or short chain alk(en)yl, branched chain alk(en)yl and $C_5$–$C_8$ cyclic ring systems;

$R^2$ thru' $R^9$ may be the same or different and may be independently selected from H, straight or branched chain lower alk(en)yl, and $C_5$–$C_8$ cyclic ring systems;

n is a number within the range of about 60 to about 120, preferably about 80, and X$^-$ is preferably acetate, but may instead be for example halide, organic carboxylate, organic sulphonate or the like.

Suitable quaternary silicone polymers of this class are described in EP-A-0 530 974.

Amino functional silicones suitable for use in the invention will typically have a mole % amine functionality in the range of from about 0.1 to about 8.0 mole %, preferably from about 0.1 to about 5.0 mole %, most preferably from about 0.1 to about 2.0 mole %. In general the amine concentration should not exceed about 8.0 mole % since we have found that too high an amine concentration can be detrimental to total silicone deposition and therefore conditioning performance.

The viscosity of the amino functional silicone is not particularly critical and can suitably range from about 100 to about 500,000 cst.

Specific examples of amino functional silicones suitable for use in the invention are the aminosilicone oils DC2-8220, DC2-81606, DC2-8466, and DC2-8950-114 (all ex Dow Corning), and GE 1149–75, (ex General Electric Silicones).

Also suitable are emulsions of amino functional silicone oils with non ionic and/or cationic surfactant.

Suitably such pre-formed emulsions will have an average amino functional silicone particle size in the shampoo composition of less than 30, preferably less than 20, more preferably less than 10 microns. We have found that reducing the particle size generally improves conditioning performance. Most preferably the average amino functional silicone particle size is less than 2 microns, ideally it ranges from 0.01 to 1 micron. Silicone emulsions having an average silicone particle size of ≦0.15 microns are generally termed microemulsions.

Particle size may be measured by means of a laser light scattering technique, using a 2600D Particle Sizer from Malvern Instruments.

Pre-formed emulsions of amino functionalised silicone are available from suppliers of silicone oils such as Dow Corning and General Electric. Specific examples include DC929 Cationic Emulsion, DC939 Cationic Emulsion, DC949 Cationic Emulsion, and the non-ionic emulsions DC2-7224, DC2-8467 and DC2-8154 (all ex Dow Corning).

An example of a quaternary silicone polymer useful in the present invention is the material K3474, ex Goldschmidt.

Emulsified, Non-amino Functionalised Silicone

The shampoo composition of the invention comprises a non-amino functionalised silicone. The silicone is insoluble in the aqueous matrix of the shampoo composition and so is present in an emulsified form, with the silicone present as dispersed particles.

The average silicone particle size of the emulsified non-amino functional silicone in the shampoo composition is less than 2 microns. Ideally it ranges from 0.01 to 1 micron. We have found that reducing the particle size in this way improves the overall conditioning performance from the shampoo composition. Particle size may be measured by means of a laser light scattering technique, using a 2600D Particle Sizer from Malvern Instruments.

Suitable silicones include polydiorganosiloxanes, in particular polydimethylsiloxanes which have the CTFA designation dimethicone. Also suitable for use in shampoo compositions of the invention are polydimethyl siloxanes having hydroxyl end groups, which have the CTFA designation dimethiconol. Also suitable for use in shampoos of the invention are silicone gums having a slight degree of cross-linking, as are described for example in WO 96/31188. These materials can impart body, volume and stylability to hair, as well as good wet and dry conditioning.

Various methods of making emulsions of particles of silicones for use in the invention are available and are well known and documented in the art. For example, emulsions may be prepared by high shear mechanical mixing of the silicone and water, or by emulsifying the silicone with water and an emulsifier (mixing the silicone into a heated solution of the emulsifier for instance), or by a combination of mechanical and chemical emulsification. A further suitable technique for preparation of emulsions of particles of silicones is emulsion polymerisation. Emulsion polymerised silicones as such are described in U.S. Pat. No. 2,891,820 (Hyde), U.S. Pat. No. 3,294,725 (Findlay) and U.S. Pat. No. 3,360,491 (Axon).

Suitable silicone emulsions for use in the invention are commercially available in a pre-emulsified form. This is particularly preferred since the pre-formed emulsion can be incorporated into the shampoo composition by simple mixing. Pre-formed emulsions are available from suppliers of silicone oils such as Dow Corning, General Electric, Union Carbide, Wacker Chemie, Shin Etsu, Toshiba, Toyo Beauty Co, and Toray Silicone Co.

The viscosity of the silicone itself (not the emulsion or the final shampoo composition) is typically at least 10,000 cst. In general we have found that conditioning performance increases with increased viscosity. Accordingly, the viscosity of the silicone itself is preferably at least 60,000 cst, most preferably at least 500,000 cst, ideally at least 1,000,000 cst. Preferably the viscosity does not exceed $10^9$ cst for ease of formulation. Viscosity can be measured by means of a glass capillary viscometer as set out further in Dow Corning Corporate Test Method CTM004 Jul. 20 1970.

Examples of suitable pre-formed emulsions include emulsions DC2-1766, DC2-1784, and microemulsions DC2-1865 and DC2-1870, all available from Dow Corning. These are all emulsions/microemulsions of dimethiconol. DC2-1766 and DC2-1784 each have an average silicone particle size in the emulsion of less than 2 microns. DC2-1865 and DC2-1870 each have an average silicone particle size in the microemulsion of less than 0.15 microns. Cross-linked silicone gums are also available in a pre-emulsified form, which is advantageous for ease of formulation. A preferred example is the material available from Dow Corning as DC X2-1787, which is an emulsion of cross-linked dimethiconol gum having an average silicone particle size in the emulsion of 0.5 microns. A further preferred example is the material available from Dow Corning as DC X2-1391, which is a microemulsion of cross-linked dimethiconol gum having an average silicone particle size in the microemulsion of 0.045 microns.

Silicone Ratios

We have found that the conditioning performance of small particle size emulsified silicone in a surfactant-based shampoo composition can be significantly boosted by the presence of an amino functionalised silicone.

The weight ratio of amino functionalised silicone to non-amino functionalised silicone is generally 1:2 or less. Suitably, the ratio of amino functionalised silicone to non-amino functionalised silicone ranges from 1:2 to 1:20, preferably 1:3 to 1:20, more preferably 1:3 to 1:8, optimally around 1:4.

Silicone Levels

The total amount of silicone (amino functional and non-amino functional) incorporated into the shampoo compositions of the invention depends on the level of conditioning desired and the material used. A preferred amount is from 0.01 to about 10% by weight of the total composition although these limits are not absolute. The lower limit is determined by the minimum level to achieve conditioning and the upper limit by the maximum level to avoid making the hair and/or skin unacceptably greasy.

We have found that a total amount of silicone of from 0.3 to 5%, preferably 0.5 to 3%, by weight of the total composition is a suitable level.

Cationic Deposition Polymer

A cationic deposition polymer is a preferred ingredient in shampoo compositions of the invention, for enhancing conditioning performance of the shampoo. By "deposition polymer" is meant an agent which enhances deposition of the silicone component from the shampoo composition onto the intended site during use, i.e. the hair and/or the scalp.

The deposition polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic nitrogen-containing group will generally be present as a substituent on a fraction of the total monomer units of the deposition polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range. Suitable cationic deposition polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–C3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic deposition polymers can comprise mixtures of monomer units derived from amine- and/or quaternary ammonium-substituted monomer and/or compatible spacer monomers.

Suitable cationic deposition polymers include, for example:

copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylamino-ethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo- and co-polymers of unsaturated carboxylic acids having from 3 to 5 carbon atoms, (as described in U.S. Pat. No. 4,009,256);

cationic polyacrylamides(as described in WO95/22311). Other cationic deposition polymers that can be used include cationic polysaccharide polymers, such as cationic cellulose derivatives, cationic starch derivatives, and cationic guar gum gerivatives.

Cationic polysaccharide polymers suitable for use in compositions of the invention include those of the formula:

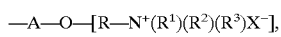

$$-A-O-[R-N^+(R^1)(R^2)(R^3)X^-],$$

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Aimerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (Commercially available from Rhodia (formerly Rhone-Poulenc) in their JAGUAR trademark series).

Examples are JAGUAR C13S and JAGUAR CB289, which have a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic deposition polymer is selected from cationic cellulose and cationic guar derivatives. Particularly preferred deposition polymers are JAGUAR C13S, JAGUAR CB289, JAGUAR C15, JAGUAR C17 and JAGUAR C16 and JAGUAR C162.

The cationic deposition polymer will generally be present at levels of from 0.001 to 5%, preferably from about 0.01 to 1%, more preferably from about 0.02% to about 0.5% by weight of the total composition.

Other Ingredients

The shampoo composition of the invention may further comprise from 0.1 to 5% by weight of the total composition of a silicone suspending agent. Examples are polyacrylic acids, cross linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbonol 980. An example of a suitable copolymer of a carboxylic acid containing a monomer and acrylic acid esters is Carbopol 1342. All Carbopol materials are available from Goodrich and Carbopol is a trade mark.

Suitable cross linked polymers of acrylic acid and acrylate esters are Pemulen TR1 or Pemulen TR2. A suitable heteropolysaccharide gum is xanthan gum, for example that available as Kelzan mu.

Compositions of this invention may contain any other ingredient normally used in hair treatment formulations. These other ingredients may include viscosity modifiers, preservatives, colouring agents, polyols such as glycerine and polypropylene glycol, chelating agents such as EDTA, antioxidants, fragrances, and sunscreens. Each of these ingredients will be present in an amount effective to accomplish its purpose. Generally these optional ingredients are included individually at a level of up to about 5% by weight of the total composition.

Preferably, compositions of this invention also contain adjuvants suitable for hair care. Generally such ingredients are included individually at a level of up to 2%, preferably up to 1%, by weight of the total composition.

Among suitable hair care adjuvants, are:
(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine.

(ii) hair fibre benefit agents. Examples are:

ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

The invention is further illustrated by way of the following non-limitative Examples:

EXAMPLES

Example 1

A shampoo composition was prepared by mixing the following components in the amounts stated:

| Ingredient | % wt |
|---|---|
| Sodium lauryl sulphate (2EO) | 14.0 |
| Cocamidopropyl betaine | 2.0 |
| Non-amino functionalised silicone[1] | 1.5 |
| Sodium chloride | 1.5 |
| Amino functionalised silicone[2] | 0.5 |
| Carbopol 980[3] | 0.4 |
| Jaguar C13S[4] | 0.1 |
| Preservative, perfume, colour | q.s. |
| Water to | 100.0 |

[1]Non-amino functionalised silicone was included as DC2-1784 from Dow Corning Ltd., an emulsion (50% a.i.) of dimethiconol (1 million cst, 0.5 micron particle size) in anionic surfactant (TEA-dodecylbenzenesulfonate).
[2]Amino functionalised silicone was included as DC929 from Dow Corning Ltd., an emulsion (35% a.i.) of amodimethicone in cationic surfactant (tallowtrimonium chloride) and nonionic surfactant (nonoxynol-10).
[3]Carbopol 980 is a cross-linked polyacrylate available from B F Goodrich.
[4]Jaguar C13S is guar hydroxypropyltrimonium chloride available from Rhodia (formerly Rhone-Poulenc)

Example 2 and Comparative Example A

Two shampoo compositions were made up having ingredients as shown in the following Table:

| | % weight | |
|---|---|---|
| INGREDIENT | Comparative Example A | Example 2 |
| Sodium lauryl ether sulphate (2EO) | 14.0 | 14.0 |
| Cocamidopropyl betaine | 2.0 | 2.0 |
| Jaguar C13S | 0.1 | 0.1 |
| Pearliser[5] | 6.0 | 6.0 |
| Formalin | 0.1 | 0.1 |
| DC 949[6] | 1.0 | 1.0 |
| DC 200 (60,000 cst)[7] | 2.0 | — |
| X2-1766[8] | — | 2.0 |
| NaCl | 0.9 | 0.9 |
| H$_2$O | to 100 | to 100 |

[5]EUPERLAN PK3000, ex Henkel
[6]An emulsion (35% a.i.) of aminoethylamindpropyl dimethylsiloxane emulsified with alkyltrimethylammonium chloride and polyethoxylated tridecylalcohol, ex Dow Corning
[7]Dimethicone fluid, viscosity 60,000 cst, ex Dow Corning. (Incorporated into the shampoo composition as neat fluid)
[8]An emulsion (60% a.i.) of dimethiconol (1 million cst, 0.5 micron particle size) in anionic surfactant (sodium lauryl sulphate), ex Dow Corning The shampoos of Example 2 and Comparative Example A were subjected to a panellist evaluation for various wet and dry conditioning attributes. The panellist preferences are shown in the following Table:

| Attribute | Example 2 | Comparative Example A |
|---|---|---|
| WET FEEL | | |
| smoothness | 79 | 21 |
| ease of comb | 83 | 17 |
| DRY FEEL | | |
| smoothness | 75 | 25 |
| ease of comb | 83 | 17 |
| lack of fly-away | 85 | 15 |

Clearly the composition of the invention (with small particle size silicone and amino functionalised silicone) outperformed the composition of the Comparative Example over all attributes tested.

What is claimed is:

1. An aqueous shampoo composition comprising, in addition to water:
   I) at least one surfactant chosen from anionic, nonionic, zwitterionic, or amphoteric surfactants or mixtures thereof;
   II) an emulsion of amodimethicone in cationic surfactant and nonionic surfactant; and
   ll) an insoluble emulsified non-amino functional silicone which is an emulsion of dimethiconol (1 million centistokes) having an average particle size of less than 2 microns in sodium lauryl sulphate.

2. A shampoo composition according to claim 1, in which the emulsified non-amino functional silicone has an average silicone particle size in the shampoo composition of from 0.01 to 1 micron.

3. A shampoo composition according to claim 1, which the weight ratio of amino functionalized silicone (ii) to non-amino functionalized silicone (iii) is 1:2 or less.

4. A shampoo composition according to claim 1, in which the amino functional silicone has a mole % amine functionality in the range of from about 0.1 to about 8.0 mole %.

5. A shampoo composition according to claim 1, in which the total amount of silicone is from 0.3 to 5%, by weight of the total shampoo composition.

6. A shampoo composition according to claim 1, further comprising from 0.001 to 5% by weight of the total shampoo composition of a cationic deposition polymer selected from cationic cellulose and cationic guar derivatives.

7. A shampoo composition according to claim 4, in which the amino functional silicone has a mole % amine functionality in the range of from about 0.1 to about 5.0 mole %.

8. A shampoo composition according to claim 4, in which the amino functional silicone has a mole % amine functionality in the range of from about 0.1 to about 2.0 mole %.

9. A shampoo composition in accordance with claim 5, in which the total amount of silicone is from 0.5 to 3% by wt. of the total shampoo composition.

10. A method for cleansing hair which comprises contacting said hair with an effective amount of the composition according to claim 1.

11. A shampoo composition according to claim 1, wherein the weight ratio of amino functionalized silicone (ii) to non-amino functionalized silicone (iii) is 1:2 to 1:20.

12. A shampoo composition in accordance with claim 1, wherein the weight ratio of amino functionalized silicone (ii) to non-amino functionalized silicone (iii) is 1:3 to 1:20.

13. A shampoo composition according to claim 1, wherein the weight ratio of amino functionalized silicone (ii) to non-amino functionalized silicone (iii) is 1:3 to 1:8.

14. A shampoo composition according to claim 1, wherein the weight ratio of amino functionalized silicone (ii) to non-amino functionalized silicone (iii) is about 1:4.

* * * * *